United States Patent

Wheatley et al.

(10) Patent No.: US 10,178,950 B2
(45) Date of Patent: Jan. 15, 2019

(54) IMAGING PROBES AND ASSOCIATED DEVICES, SYSTEMS, AND METHODS UTILIZING AN ELASTOMERIC OPTICAL ELEMENT

(71) Applicant: Novartis AG, Basel (CH)

(72) Inventors: Barry L. Wheatley, Oceanside, CA (US); Kambiz Parto, Laguna Niguel, CA (US)

(73) Assignee: Novartis AG, Basel (CH)

( * ) Notice: Subject to any disclaimer, the term of this patent is extended or adjusted under 35 U.S.C. 154(b) by 754 days.

(21) Appl. No.: 14/137,568

(22) Filed: Dec. 20, 2013

(65) Prior Publication Data

US 2015/0173605 A1    Jun. 25, 2015

(51) Int. Cl.
| | |
|---|---|
| A61B 5/05 | (2006.01) |
| A61B 3/10 | (2006.01) |
| A61B 3/12 | (2006.01) |
| G02B 3/00 | (2006.01) |
| G02B 26/10 | (2006.01) |
| A61B 5/00 | (2006.01) |

(52) U.S. Cl.
CPC .............. *A61B 3/102* (2013.01); *A61B 3/12* (2013.01); *A61B 5/0084* (2013.01); *G02B 3/0087* (2013.01); *G02B 26/10* (2013.01)

(58) Field of Classification Search
USPC .......................................................... 600/425
See application file for complete search history.

(56) References Cited

U.S. PATENT DOCUMENTS

| | | | |
|---|---|---|---|
| 4,638,800 A  * | 1/1987 | Michel | 606/14 |
| 5,093,719 A  * | 3/1992 | Prescott | 348/65 |
| 6,485,413 B1 * | 11/2002 | Boppart et al. | 600/160 |
| 6,599,317 B1 * | 7/2003 | Weinschenk et al. | 623/6.34 |
| 7,261,687 B2 | 8/2007 | Yang | |
| 7,364,543 B2 | 4/2008 | Yang et al. | |
| 7,616,986 B2 | 11/2009 | Seibel et al. | |

(Continued)

FOREIGN PATENT DOCUMENTS

| | | |
|---|---|---|
| JP | S60-176017 A | 9/1985 |
| WO | WO 2012/166116 | 12/2012 |

OTHER PUBLICATIONS

International Search Report and Written Opinion issued for PCT/US2014/069101, dated Mar. 16, 2015, 10 pgs.

(Continued)

*Primary Examiner* — Joel F Brutus

(57) ABSTRACT

The imaging probe can comprise a housing, having a proximal region configured to be coupled to an optical cable; a cannula, extending from a distal region of the housing; an optical guide, positioned partially in the housing and partially in the cannula, configured to receive an imaging light from the cable in the proximal region of the housing, and to guide the imaging light towards a distal end of the cannula; an optical focusing element, configured to receive the imaging light from the optical guide, and to emit a focused imaging light; an elastomeric optical element, configured to receive the focused imaging light from the optical focusing element, and to be deformable to redirect the focused imaging light; and an actuator system, configured to deform the elastomeric optical element to redirect the focused imaging light.

27 Claims, 8 Drawing Sheets

(56) References Cited

U.S. PATENT DOCUMENTS

| | | |
|---|---|---|
| 2004/0042097 A1 | 3/2004 | Murnan et al. |
| 2010/0282954 A1* | 11/2010 | Hendriks et al. .......... 250/227.2 |
| 2011/0144228 A1* | 6/2011 | Ravi ............................. 523/106 |
| 2012/0190921 A1* | 7/2012 | Yadlowsky et al. .......... 600/106 |
| 2013/0084420 A1 | 4/2013 | Auciello et al. |
| 2013/0158392 A1 | 6/2013 | Papac et al. |

OTHER PUBLICATIONS

Monson, T.C. et al. "High Refractive Index TiO2 Nanoparticle/Silicone Composites." National Nuclear Security Administration Physical, Chemical, & Nano Sciences Center Research Briefs (2008): 46-47. Web. Feb. 3, 2012.

\* cited by examiner

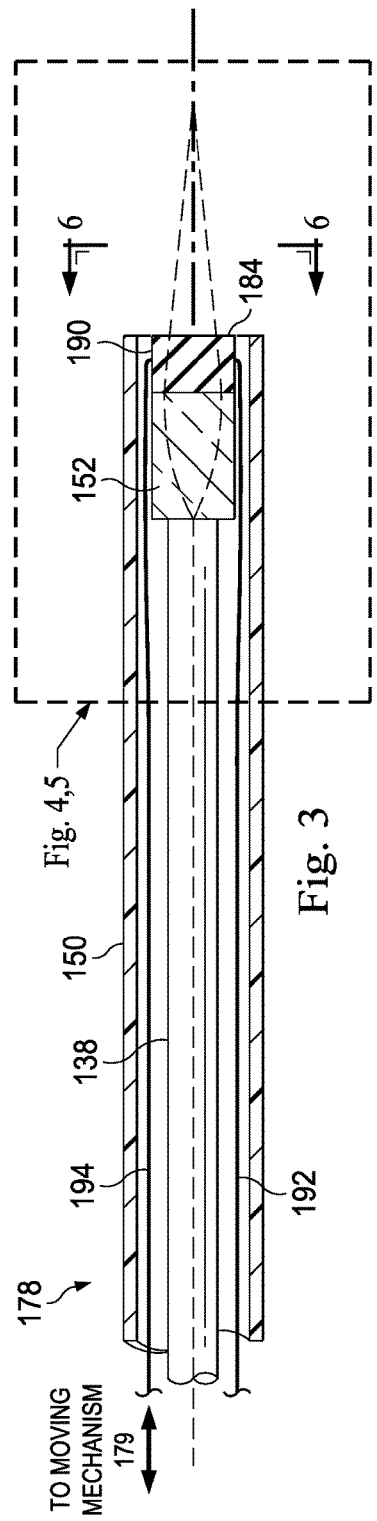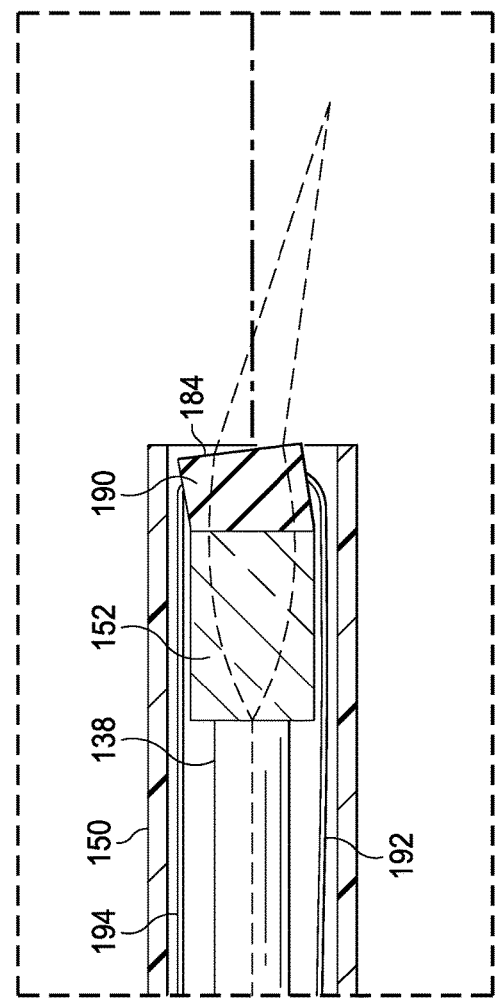

IMAGING PROBES AND ASSOCIATED DEVICES, SYSTEMS, AND METHODS UTILIZING AN ELASTOMERIC OPTICAL ELEMENT

TECHNICAL FIELD

Embodiments disclosed herein are related to devices, systems, and methods for scanning tissue with an optical coherence tomography (OCT) imaging probe, and more particularly, to devices, systems, and methods that utilize an OCT imaging probe having an elastomeric optical element for ophthalmic imaging.

BACKGROUND

Optical Coherence Tomography (OCT) systems can be used in ophthalmology to generate images of tissue layers. These OCT systems often include an OCT probe that is inserted into the eye to visualize an ophthalmic tissue, such as the retina. The OCT probes often include a handle, connected to the rest of the OCT imaging system by an optical cable and a protruding cannula that is inserted into the patient tissue.

In use, a generated light beam is split into an imaging light beam and a reference light beam. The imaging light beam is guided by the imaging probe at the target tissue. A portion of this imaging light is reflected from a range of depths of the target tissue and is collected through the same probe. The reflected and collected imaging light beam is then interfered with the reference beam, and from the interference an OCT image of the target in a range of depths is generated.

Some OCT systems create an in-depth image corresponding to a target spot: such an image is typically called an A-scan. Other OCT systems are built to scan through a set of target spots and create in-depth images corresponding to these scanned spots. These in-depth images can be assembled into a so-called B-scan, in essence, an XZ or YZ cross-sectional image of the target tissue in a lateral (X or Y) and an in-depth (Z) direction.

Some probes can scan the imaging beam by moving an optical fiber back and forth within the distal region of the cannula. However, the small diameter of the cannula makes it difficult to move the fiber back and forth. Further, the small space available within the imaging probe limits the types of actuators that can move the fiber. Finally, since in several types of usage the OCT probes are disposed after the procedure, their manufacture must be inexpensive.

Accordingly, there is a need for improved devices, systems, and methods that utilize an OCT probe for scanning an imaging beam over a target tissue, including ophthalmic OCT probes that address one or more of the needs discussed above.

SUMMARY

Embodiments disclosed herein are related to devices, systems, and methods that utilize an elastomeric optical element configured to selectively deform to change a direction of a focused imaging light.

Consistent with some embodiments, an imaging probe is provided. The imaging probe can comprise a housing, having a proximal region configured to be coupled to an optical cable; a cannula, extending from a distal region of the housing; an optical guide, positioned partially in the housing and partially in the cannula, configured to receive an imaging light from the cable in the proximal region of the housing, and to guide the imaging light towards a distal end of the cannula; an optical focusing element, configured to receive the imaging light from the optical guide, and to emit a focused imaging light; an elastomeric optical element, configured to receive the focused imaging light from the optical focusing element, and to be deformable to redirect the focused imaging light; and an actuator system, configured to deform the elastomeric optical element to redirect the focused imaging light.

Consistent with some embodiments, an imaging system is provided. The imaging system can comprise an optical coherence tomography imaging system comprising an imaging light source configured to generate an imaging light; an optical cable, configured to guide the imaging light; a housing, having a proximal region configured to be coupled to the optical cable; a cannula, extending from a distal region of the housing; an optical guide, configured to receive an imaging light from the cable in the proximal region of the housing, and to guide the imaging light towards a distal end of the cannula; a, optical focusing element, configured to receive the imaging light from the optical guide, and to emit a focused imaging light; an elastomeric optical element, configured to receive the focused imaging light from the optical focusing element, and to be deformable to redirect the focused imaging light; and an actuator system, configured to deform the elastomeric optical element to redirect the focused imaging light.

Consistent with some embodiments, a method of imaging an ophthalmic target with an imaging probe is provided, the method comprising: guiding an imaging light to an optical focusing element inside a cannula of the imaging probe with an optical guide; focusing the imaging light with the optical focusing element; receiving the focused imaging light by an elastomeric optical element; redirecting the focused imaging light to a target spot by deforming the elastomeric optical element with an actuator system; and scanning the redirected focused imaging light along a scanning pattern by sequentially deforming the elastomeric optical element with the actuator system.

Additional aspects, features, and advantages of the present disclosure will become apparent from the following detailed description.

BRIEF DESCRIPTION OF THE DRAWINGS

FIG. 3 illustrates a cross-sectional view of a distal portion of an imaging probe.

FIGS. 4A-B illustrate a scanning operation of the imaging probe of FIG. 3.

Figure 1:
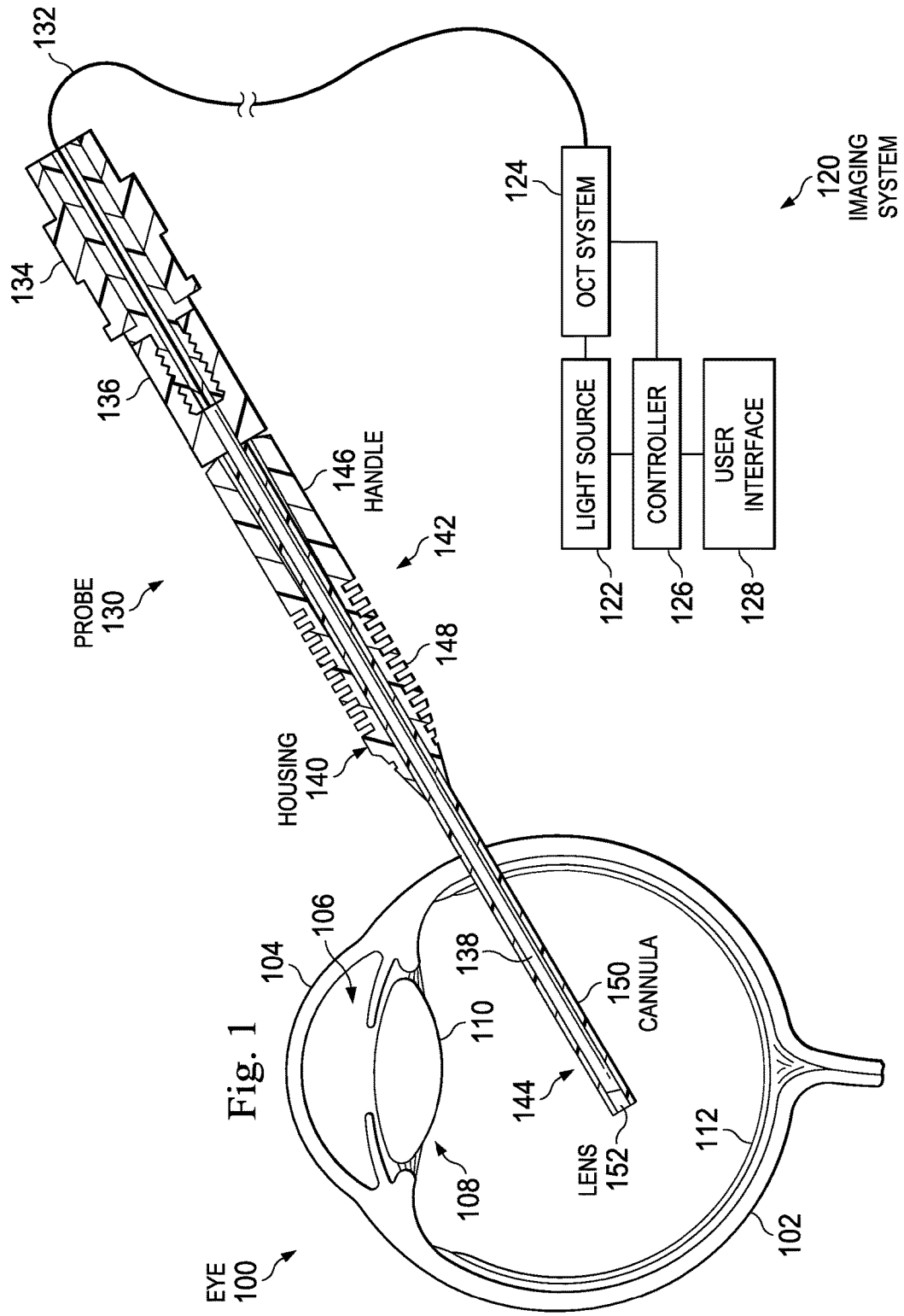
FIG. 1 illustrates an eye under treatment and an exemplary OCT imaging system.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure relates generally to OCT probes, OCT systems, and methods that scan tissue to obtain an OCT image. The OCT imaging probe can include a handle, coupled to a cable that guides the imaging light from a light source to the handle. A cannula can extend from the distal end of the handle, configured to invasively penetrate patient tissue, such as the globe of an eye. The cannula can house an optical fiber, guiding light to a lens at its distal end. The fiber directs the imaging light through the lens to the target and captures the reflected light, coming from the target through the lens.

The cannula has a small cross section because it is desirable to create an incision for its insertion as small as possible. Therefore, the diameter of the fiber has to be small enough to fit into the very thin cannula, imposing strong upper bounds on the fiber's diameter. In addition, there is a lower bound on the fiber diameter as well, set by the wavelength $\lambda$ of the OCT imaging light. Typical values of $\lambda$ in OCT systems include 850 nm, 1060 nm or 1350 nm, and the minimal fiber diameter is set by this wavelength. The above upper and lower bounds can combine into a narrow design range for the fiber diameter. In addition, the fiber needs to leave space for a portion of the actuator mechanism as well in the cannula.

A second important consideration is that to scan a line or an area of tissue rather than imaging merely a point, the imaging light can be redirected to scan across the desired line or area. In some designs, the scanning is achieved by moving the distal end of the fiber relative to the distal lens. Since the fiber is to be moved within the cannula, its diameter must be even smaller than the lumen of the cannula to allow room for the fiber's movement. And since the diameter of the fiber is smaller than that of the distal lens, the imaging beam propagates through only a portion of the lens surface, making the numerical aperture of the focused imaging beam smaller compared to designs where the fiber has the same diameter as the lens, allowing the imaging beam to propagate through the entire lens surface. In the designs where the fiber is movable relative to the lens, the numerical aperture is smaller and therefore the focal spot is bigger, possibly impacting the sharpness of the OCT image.

Finally, in systems where the fiber moves relative to the lens, the fiber-lens optical coupling varies during scanning, thus the coupling may not be optimal for periods of the scanning operations.

In exemplary scanning imaging probes described herein the fiber can be attached to a larger fraction of the proximal surface of the lens, possibly to the entire proximal lens surface. Such designs make the imaging beam broader, thus propagating through the entire proximal surface of the lens. Thus, in these designs the numerical aperture of the imaging beam is increased relative to the moving fiber designs. One of the consequences is that the focusing of the imaging beam improves as well.

These designs provide the scanning functionality not by moving the fiber, but by attaching a deformable elastomeric optical element to a distal end of the lens. The elastomeric optical element can be deformed by an actuator system to scan a direction of the focused imaging light to scan along a 1D or 2D pattern. The actuator system can include an actuator with one or more arms with distal ends attached to respective portions of the elastomeric optical element. Proximal ends of the actuating arms can be moved to cause the distal ends of the actuating arms to deform the respective portions of the elastomeric optical element. The rest of the actuator system can be positioned in the handle of the OCT probe where somewhat more space is available. These designs can impart repeatable deformation to the elastomeric optical element of the OCT probe, enabling a useful optical scanning function, and can be manufactured in a cost-effective manner.

Designs that scan the imaging light by deforming the elastomeric optical element overcome one or more of the problems or limitations of previous approaches, including the following. (1) These designs can incorporate an optical fiber with a size larger than scanning fiber designs, thus relaxing the upper bound on the fiber diameter. (2) They preserve the orientation of the optical fiber with respect to the distal lens, thus allowing the formation of an optimalized fiber-lens optical coupling. (3) The larger fiber diameter increases the numerical aperture of the imaging probe. (4) Finally, these designs improve the focusing and thus the image clarity and resolution.

FIG. 1 is a diagrammatic schematic view of an arrangement illustrating aspects of the present disclosure. In particular, an eye 100 under treatment is shown. The eye 100 includes sclera 102, a cornea 104, an anterior chamber 106, and a posterior chamber 108. A capsular bag 110 is illustrated in the posterior chamber 108. The eye 100 further includes a retina 112.

An exemplary imaging system 120 is also illustrated in FIG. 1. As discussed in greater detail below, imaging system 120 is configured to image portions of the eye 100, such as the retina 112. The imaging system 120 can include a light source 122, an optical coherence tomography (OCT) system 124, a controller 126, a user interface 128, and an imaging probe 130. The light source 122 is configured to provide imaging light that will be directed onto the target biological tissue by the imaging probe 130. The light source 122 can be made up of super-luminescent diodes, ultra-short pulsed lasers, or supercontinuum lasers that provide relative long wavelength light, such as between 700 nm and 1400 nm, between 900 nm and 1200 nm, or between 1000 nm and 1100 nm. A superluminescent diode (SLED) laser with a wavelength of between 800-900 nm can have a focal spot of approximately 20 microns. Imaging light reflected from the target biological tissue and captured by the imaging probe 130 is utilized to generate images of the target biological tissue.

The OCT system 124 is configured to split the imaging light received from the light source 122 into the imaging beam that is directed onto the target biological tissue by the imaging probe 130 and a reference beam that can be directed onto a reference mirror. The OCT system 124 can be a spectral domain or a time domain system. The OCT system 124 is further configured to receive the imaging light reflected from the target biological tissue and captured by the imaging probe 130. The interference pattern between the reflected imaging light and the reference beam is utilized to generate images of the target biological tissue. Accordingly, the OCT system 124 can include a detector configured to detect the interference pattern. The detector can include Charge-Coupled Detectors (CCDs), pixels, or an array of any other type of sensor(s) that generate an electric signal based on detected light. Further, the detector can include a two-dimensional sensor array and a detector camera.

The controller 126 can include a processor and memory, which may include one or more executable programs for controlling aspects of the light source 122, the user interface 128, and/or the imaging probe 130, and for executing and performing functions and processes to carry out an OCT imaging procedure. For example, the controller 126 can be configured to control an actuation system of the imaging probe 130, configured to scan the imaging beam across the target biological tissue in some implementations.

One or more of the light source 122, the OCT system 124, the controller 126, and the user interface 128 can be implemented in separate housings communicatively coupled to one another or within a common console or housing. For example, in some implementations the light source 122, the OCT system 124, and the controller are positioned within a console that is communicatively coupled to the user interface 128. The user interface 128 can be movable or form part of the console. Further, the user interface 128, or at least part(s) thereof, can be separate from the console. The user interface 128 can include a display configured to present images to a user or a patient, and display tissue scanned by the imaging probe 130 during an OCT imaging procedure. The user interface 128 can also include input devices or systems, including by way of non-limiting example, a keyboard, a mouse, a joystick, a touchscreen, dials, and buttons, among other input devices.

The imaging probe 130 can be in optical communication with OCT system 124. An optical cable 132 can connect the imaging probe 130 to the OCT system 124 and/or the controller 126. The optical cable 132 can include optical fiber(s), electrical conductor(s), insulator(s), shield(s), and/or other features configured to facilitate optical and/or electrical communication between the imaging probe 130 and the OCT system 124 and/or the controller 126. Further, it is understood that optical cable 132 can include multiple, separate cables. For example, in some instances an optical cable connects the imaging probe 130 to OCT system 124 and a separate electrical cable connects the imaging probe 130 to controller 126.

The imaging probe 130 can receive the imaging light guided by the optical cable 132 from the light source 122. The received imaging light beam can be received by an optical guide or fiber 138 and guided to a distal lens 152 at the distal end region of a cannula 150 to be focused and directed to the target region.

The imaging probe 130 can be in electrical communication with the controller 126. In that regard, the controller 126 can control an actuation system of the imaging probe 130 via electrical signals sent to the imaging probe 130 in order to cause the actuation system to scan the imaging beam across the target biological tissue.

In the illustrated embodiment, the cable 132 can terminate in a connector 134 that is configured to facilitate removable coupling of the imaging probe 130 to the cable 132. The connector 134 can be configured to selectively engage with a connector 136 associated with the imaging probe 130 to facilitate mechanical, optical, and/or electrical coupling of the imaging probe 130 to the cable 132. For example, an optical fiber, or optical guide 138, extending along the length of the imaging probe 130, can be optically coupled to the optical cable 132 and thus to the OCT system 124 via coupling of the connectors 134 and 136. The optical fiber/guide 138 can be a single fiber or a fiber bundle.

In some embodiments, only one connector, such as connector 134, is present. In the illustrated embodiment, the connector 136 is configured to threadingly engage with the connector 134. However, it is understood that any type of selective engagement feature(s) or connectors can be utilized to couple the imaging probe 130 to the cable 132, including without limitation press fit, luer lock, threads, and combinations thereof, among other connection types. The selective engagement of the connector 136 with the connector 134 allows the entire probe 130 to be disposable, configured for use in a single procedure, while the connector 134 and cable 132 can be reusable components that can be sterilized (e.g., using autoclave procedures) and used in multiple procedures.

In other embodiments, the optical cable 132 can be directly coupled into the imaging probe 130, and the connectors 134 and 136 can be positioned in the OCT system 124. In these embodiments, both the probe 130 and the optical cable 132 can be disposable. An aspect of such embodiments is that no reusable part of the imaging system 120 requires sterilization between procedures.

The imaging probe 130 can be sized and shaped to be handled by a surgeon. The imaging probe 130 can include a housing 140 having a proximal portion 142. The proximal portion 142 of the housing 140 can be sized and shaped for handheld grasping by the surgeon. For example, the proximal portion 142 of the housing 140 can define a handle 146. The handle 146 can be sized and shaped for grasping by a single hand of the user. Further, the handle 146 can include a textured surface 148 (e.g., roughened, knurled, projections/recesses, tapers, other surface features, and/or combinations thereof) to enhance the user's grip on the handle 146. In use, the surgeon can control the position of the cannula 150 extending from the housing 140 by maneuvering the handle 146 such that the imaging light beam is directed towards the target biological tissue.

The cannula 150 can be sized and shaped for insertion into the eye 100 to be treated. For example, the cannula 150 can be sized and shaped for insertion through the sclera 102 of the eye 100 to facilitate imaging of the retina 112. The cannula 150 can be integrally formed with the handle 146. In such designs, the handle 146 and the cannula 150 can be viewed as a proximal portion 142 and a distal portion 144 of an integrated probe 130. Alternatively, the cannula 150 and the handle 146 can be separate components that are secured to one another.

The optical cable 132 can guide the imaging light from the OCT imaging system 120 to the imaging probe 130, where it can couple the imaging light into the optical guide of optical fiber 138. The optical guide/fiber 138 can guide the imaging light to a distal region of the cannula 150. In some embodiments, the optical cable 123 and the optical guide/fiber 138 can be portions of one continuous optical guidance system. The optical fiber/guide 138 can be positioned partially in the housing 140 and partially in the cannula 150.

In this distal region of the cannula 150 an optical focusing element 152 can be secured. The optical focusing element 152 can be configured to focus the imaging light received from the optical guide 138 onto the target biological tissue, such as the retina 112. This distal region of the cannula 150 will be described in greater detail in relation to FIGS. 3-13.

As will be discussed in greater detail below, an elastomeric optical element can be selectively deformed by an actuator system disposed within the imaging probe 130 to cause the imaging beam to scan across a portion of the target biological tissue. FIGS. 3-13 illustrate various exemplary embodiments of actuator systems in accordance with the present disclosure. In that regard, it is understood that the actuator systems of the present disclosure can be positioned within the handle 146, within the cannula 150, and/or combinations thereof to selectively deform the elastomeric optical element to scan the focused imaging light across a desired scan pattern. In some embodiments, the actuator system can be configured to actuate the elastomeric optical element 190 to scan the focused imaging light along a scanning pattern having a linear extent between 1 mm and 5 mm at a distance between 5 mm and 10 mm from a distal end of the elastomeric optical element.

The distance of the focal point of the imaging beam from the distal end of the imaging probe 130 can be determined by the optical focusing element 152. Accordingly, the optical power of the optical focusing element 152 can be selected to have a focus depth corresponding to a likely distance of the distal end of the imaging probe 130 from the target biological tissue during use. For example, in some implementations of the imaging probe 130 for retinal imaging, the focal power of the optical focusing element 152 is selected such that the focal point of the imaging beam can be between 1 mm and 20 mm, between 5 mm and 10 mm, between 7 mm and 8 mm, or approximately 7.5 mm beyond the distal end of the imaging probe 130.

Figure 2:
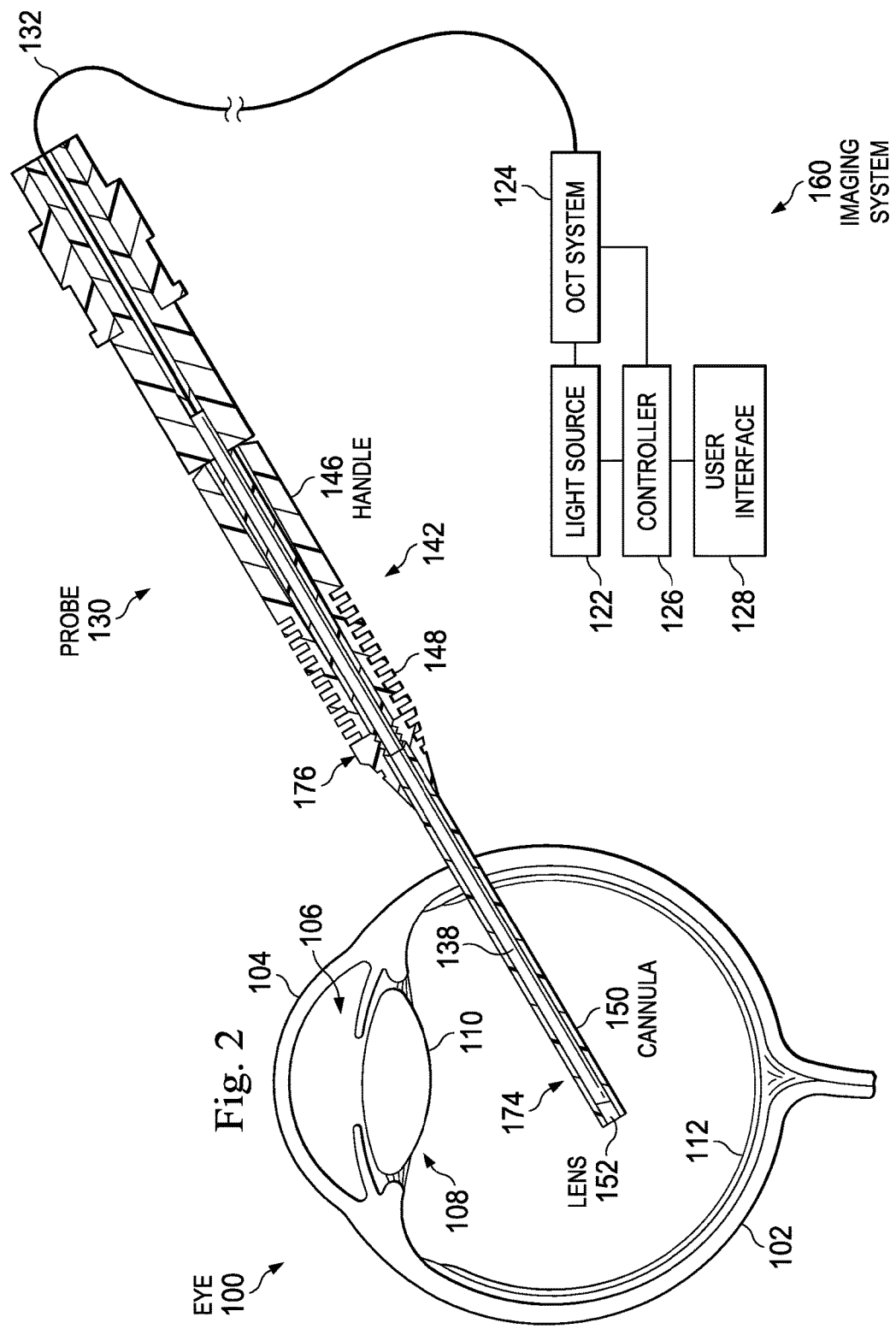
FIG. 2 illustrates an eye under treatment and an exemplary OCT imaging system.

FIG. 2 is a schematic view of an embodiment similar to that of FIG. 1. In particular, an exemplary imaging system 160 is illustrated. Similar to imaging system 120 of FIG. 1, the imaging system 160 can include the light source 122, the OCT system 124, the controller 126, the user interface 128, and the optical cable 132.

Imaging system 160 can further include an imaging probe 130. Imaging probe 130 is similar in many respects to imaging probe 130 described above. For example, the imaging probe 130 is sized and shaped to be handled by a surgeon and to protrude into a body of the patient. The imaging probe 130 includes a proximal portion 142 and a distal portion 174. The proximal portion 142 can be sized and shaped for handheld grasping by a user. For example, the proximal portion 142 can include the handle 146 having the textured surface 148 to enhance the user's grip of the imaging probe 130.

In contrast to the embodiment of the imaging probe 130 of FIG. 1, the distal portion 174 of the imaging probe 130 can be configured to be removably coupled to the proximal portion 142 of the imaging probe 130. In the illustrated embodiment, the distal portion 174 is configured to threadingly engage with the proximal portion 142 at connection 176. However, it is understood that any type of selective engagement feature(s) or connectors can be utilized to couple the proximal portion 142 to the distal portion 174 of the imaging probe 130 together, including without limitation press fit, luer lock, threads, and combinations thereof, among other connection types.

The selective engagement of the distal portion 174 with the proximal portion 142 can facilitate an optical coupling of the optical fiber 138 extending within the cannula 150 of the distal portion 174 to the OCT system 124 via optical cable 132. The cable 132 can be permanently secured to the proximal portion 142 of the imaging probe 130, as shown. Or, it can be removably coupled to the proximal portion 142, e.g., using connectors analogous to the connectors 134 and 136, described above.

The selective engagement of the distal portion 174 of the imaging probe 130 with the proximal portion 142 of the imaging probe 130 allows the distal portion 174 to be a disposable component configured for use in a single procedure, while the proximal portion 142 and cable 132 to be reusable components that can be sterilized (e.g., using autoclave procedures) and used in multiple procedures.

FIG. 3 is a stylized illustration of a cross-sectional view of an embodiment of imaging probe 130 in accordance with an aspect of the present disclosure. As shown, the optical fiber 138 can extend along the length of the imaging probe 130 through the cannula 150. The optical guide 138 can receive the imaging light at its proximal end from the optical cable 132. The distal end of the optical fiber 138 can be optically coupled to the optical focusing element 152. The optical focusing element 152 can be a lens 152, configured to focus the received imaging light and to emit a focused imaging light. In some embodiments, the optical focusing element can be a gradient index (GRIN) lens.

Additionally, some embodiments can include an elastomeric optical element 190, positioned distally to the optical focusing element 152. The elastomeric optical element 190 can be optically coupled to the optical focusing element 152 and configured to receive the focused imaging light and to be deformable to redirect the focused imaging light.

The elastomeric optical element 190 can be formed from transparent and deformable materials, such as a silicone material, an elastomer, a polymer, an epoxy, a polyurethane material, a gel, or an electro-active polymer. Further, the elastomeric optical element 190 can include nanoparticles to modulate its index of refraction. In some embodiments, the nanoparticles can include titanium dioxide (TiO2) nanoparticles to have high index of refraction n described by Monson, T. C. et al. "High Refractive Index TiO2 Nanoparticle/Silicone Composites." National Nuclear Security Administration Physical, Chemical, & Nano Sciences Center Research Briefs (2008): p. 46-47. (3 Feb. 2012).

which is hereby incorporated by reference in its entirety. In embodiments, n can be higher than that of the vitreous humor, that is close to water's 1.37. In some embodiments, the index of refraction n is between 1.4 and 10.0, between 1.4 and 3.0, or between 1.4 and 1.8.

The imaging probe 130 can include an actuator system 178 configured to selectively deform, expand, and compress the elastomeric optical element 190 to redirect, or adjust, the focused imaging beam. The actuator system 178 can include one or more actuating arms 192 and 194, positioned at least partially within the cannula 150. The actuating arms 192 and 194 of the actuator system 178 can be configured to deform the elastomeric optical element 190 to redirect and scan the focused imaging light beam along a scanning pattern.

The optical focusing element 152 can be configured to focus the imaging light received from the optical fiber 138 and to emit a focused imaging beam. Since a diameter of the optical guide 138 can be a larger fraction of a diameter of the optical focusing element 190 than in the above discussed movable fiber systems, a numerical aperture of the focused imaging light can be greater than a numerical aperture of the optical guide 138. A larger numerical aperture is capable of forming a smaller focal spot. In some embodiments, a diameter of a focal spot of the focused imaging light can be less than 50 microns.

The focused imaging beam can enter the elastomeric optical element 190 from the optical focusing element 152 and leave through a distal face 184. The distal face 184 of the elastomeric optical element 190 can be perpendicular to an optical axis of the cannula 150 when the elastomeric optical element 190 is not deformed. Or, the distal face 184 can form an oblique angle with respect to the optical axis of the cannula 150 when the elastomeric optical element 190 is deformed.

The actuator system 178 is configured to deform the elastomeric optical element 190 to change the direction of, or redirect, the focused imaging light beam to scan the focused imaging light along a scanning pattern in the target tissue. The actuator system 178 can include the actuating arms 192 and 194 expanding along a longitudinal axis of the cannula 150. The actuating arms 192 and 194 can be wires, strips, bands, or elongated thin plates, configured to be pushed or pulled at their proximal ends by a moving mechanism 179 of the actuator system 178, as further described below. In some embodiments, the actuator system 178 comprises only one actuating arm 192 that can be pushed and pulled. The distal ends of the actuating arms 192 and 194 can be attached to respective side walls of the elastomeric optical element 190.

Figure 4B:
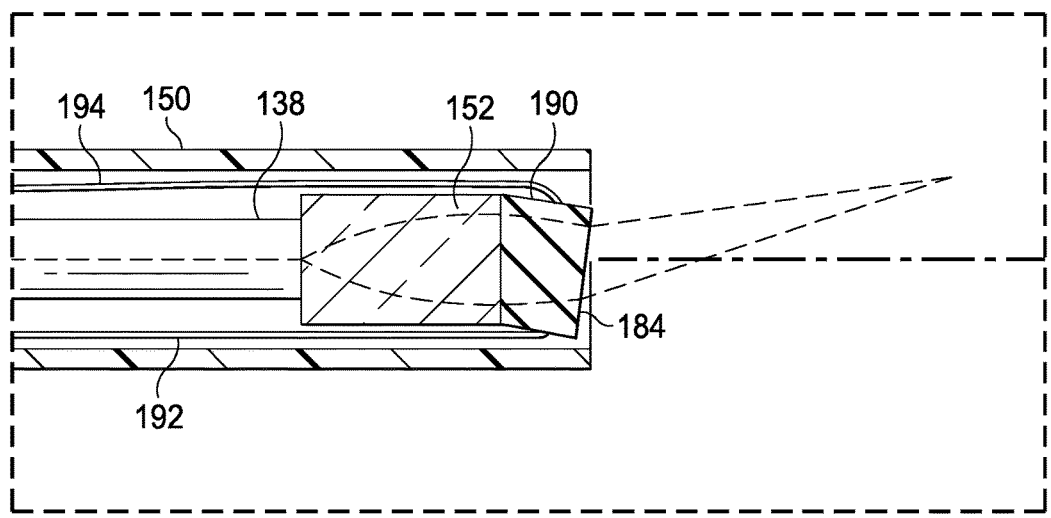

FIGS. 4A-B illustrate a scanning operation of the actuator system 178. The actuating arms 192 and 194 can be actuated to deform the elastomeric optical element 190 to change the direction of, or redirect, the focused imaging light. The moving mechanism 179 can be configured to move the two actuating arms 192 and 194 in an opposing manner so that they together deform the elastomeric optical element 190.

For example, actuating arm 194 can be pulled by the moving mechanism 179 toward the proximal end of the cannula 150 to compress a portion of the elastomeric optical element 190 that is coupled to the actuating arm 194. Further, actuating arm 192 can be pushed by the moving mechanism 179 toward the distal end of the cannula 150 to expand another portion of the elastomeric optical element 190 that is coupled to actuating arm 192. The actuation of the actuated arms 192 and 194 can tilt the distal surface 184 of the elastomeric optical element 190 upward as shown in FIG. 4A. The tilting of distal surface 184 can create a prism effect to divert, or redirect, the focused imaging light. In the case of FIG. 4A, As a result, the direction of the focused imaging light can be changed, e.g., downward as shown in FIG. 4A.

Referring now to FIG. 4B, the actuating arms 192 and 194 can be actuated to steer the focused imaging light to a different direction. For example, the actuating arm 194 can be pushed toward the distal end of the cannula 150 and the actuating arm 192 can be pulled toward the proximal end of the cannula 150 by the moving mechanism 179 to deform the elastomeric optical element 190 such that the distal surface 184 of the elastomeric optical element is tilted downward, as shown in FIG. 4B. This deformation of the elastomeric optical element 190 can redirect the focused imaging light upward, as shown in FIG. 4B. By selectively pushing and pulling the actuating arms 192 and 194, various degrees and shapes of deformation can be achieved in the elastomeric optical element 190 to result in a plurality of different directions of focused scanning light.

In other embodiments, one of the actuating arms 192 and 194 can be fixed and only one of the actuating arms can be movable. In these embodiments, the actuator mechanism 179 can actuate the elastomeric optical element 190 by pushing and pulling the movable actuating arm. Such embodiments offer simpler implementations with fewer moving parts.

In yet other embodiments, more than two actuating arms can be utilized. For example, the actuator system 178 can include 3, 4, or more actuating arms. Such implementations offer finer precision and control for the scanning operations, as well as two dimensional scanning instead of linear scanning.

The elastomeric optical element 190 can be cyclically actuated to achieve a scan. The actuator system 178 can be configured to oscillate the elastomeric optical element 190 with a frequency in the range between 0.1 Hz and about 100 kHz, or between 1 Hz and 1 kHz, or between 1 Hz and 100 Hz, although other frequency ranges, both larger and smaller, are contemplated.

Figure 5A:
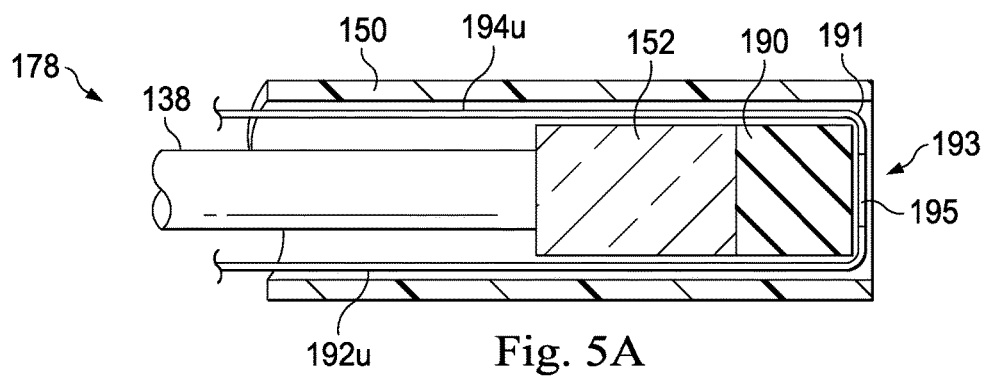
FIGS. 5A-F illustrate embodiments of the imaging probe.
Figure 5B:
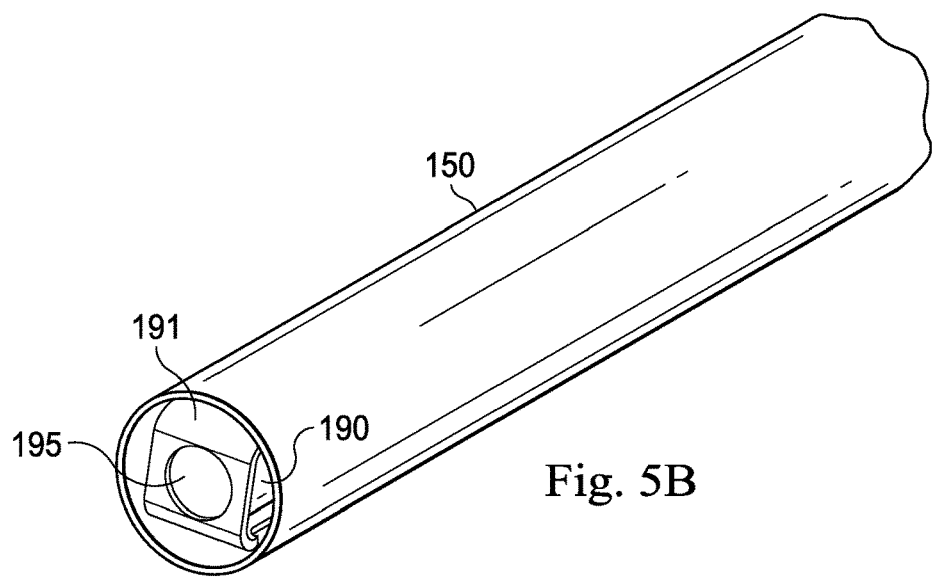
Figure 5C:
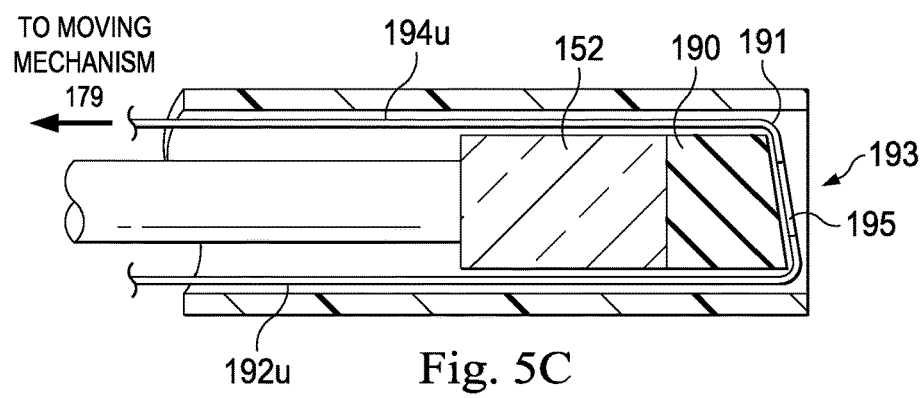

FIGS. 5A-F illustrate other embodiments of the actuator system 178. As shown in FIGS. 5A-B, in these embodiments, the actuator system 178 can include a flexible strip 191, bent into a U-shape that has two strip segments 192$u$ and 194$u$, connecting to an apex 193 of the U. One of the strip segments 192$u$ or 194$u$ is movable, in the shown figures strip segment 194$u$. Strip segments 192$u$ and 194$u$ can be embodiments of the actuating arms 192 and 194.

The apex 193 of the U can be positioned at a distal end of the cannula 150. An opening 195 can be formed at the apex 193 of the U, and a distal face of the elastomeric optical element 190 can be affixed to the apex 193 of the U at the opening 195. In some embodiments, the elastomeric optical element 190 can protrude to some degree through the opening 195. In these embodiments, the focused imaging light leaves the elastomeric optical element 190 through the opening 195. The elastomeric optical element 190 can be deformed when one or both of the strip segments 192$u$ and 194$u$ is actuated.

The operation of embodiments is shown in FIGS. 5C-F. In this embodiment, the strip segment 194$u$ is movable and the strip segment 192$u$ is fixed to an inner side of the cannula 150. The moving mechanism 179 is configured to move the movable strip segment 194$u$ to deform the elastomeric optical element 190. As shown before in FIGS. 4A-B, the tilting of the distal face of the elastomeric element 190 can redirect the focused imaging light. A continuous or cyclic operation of the moving mechanism can scan the focused imaging light along a scanning pattern, such as a scanning line.

Figure 5D:
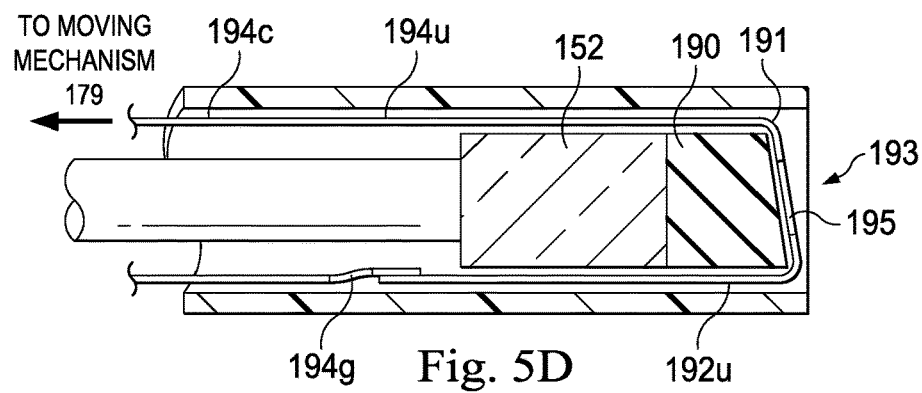

FIG. 5D shows in a side view that in some embodiments of the actuator system 178, a proximal portion of the movable strip segment 194$u$ can be expanded into an inner actuator cannula 194$c$ that is movable within the cannula 150. A groove 194$g$ can be formed in the side of the inner actuator cannula 194$c$ to accommodate the fixed strip segment 192$u$. This accommodation can achieve that the actuator 178 has the same diameter along most of its distal portion, making the assembly of the imaging probe 130 easier. In operation, the moving mechanism 179 can move the inner actuator cannula 194$c$. Since the fixed strip segment 192$u$ is fixed to an inner wall of the cannula 150, the U shaped flexible strip 191 will flex and bend at the apex region 193, tilting the distal face of the elastomeric optical element 190.

Figure 5E:
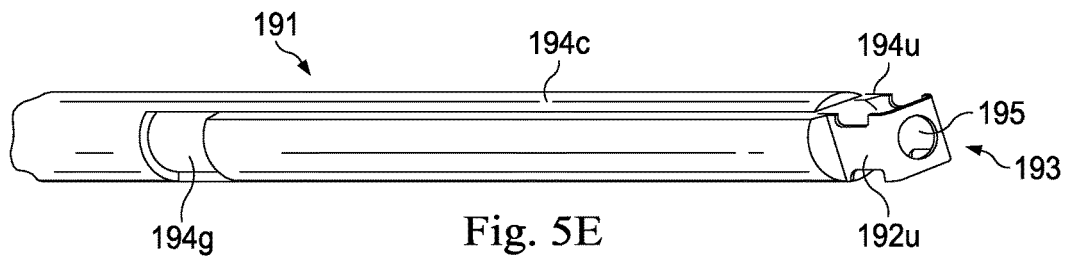

FIG. 5E illustrates an embodiment related to FIG. 5D from a perspective view without the cannula 150, the optical guide 138, the optical focusing element 152 and the elastomeric optical element 190, for clarity. Here, the movable strip segment 194u is expanded into the inner actuator cannula 194c very close to the apex 193. The groove 194g can be quite long and the fixed strip segment 192u can extend to a considerable length.

Figure 5F:
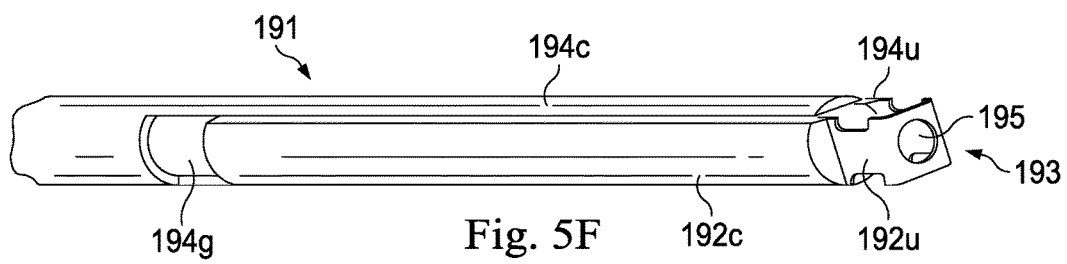

FIG. 5F shows an alternative description of essentially the same embodiment. The movable strip segment 194u and the fixed strip segment 192u can be viewed as short elements. The movable strip segment 194u can be coupled to the inner actuator cannula 194c and the fixed strip segment 192u can be coupled to a fixed inner cannula segment 192c that is fixed to an inner wall of the cannula 150. The fixed inner cannula segment 192c can be accommodated in the groove 194g formed in the inner actuator cannula 194c.

In all of the above embodiments, the moving mechanism 179 can be a wide variety of known mechanisms, including an electromotor, a piezo-electric actuator, a hydraulically operated mechanism, an electromagnetically actuated mechanism, or equivalents.

Figure 6:
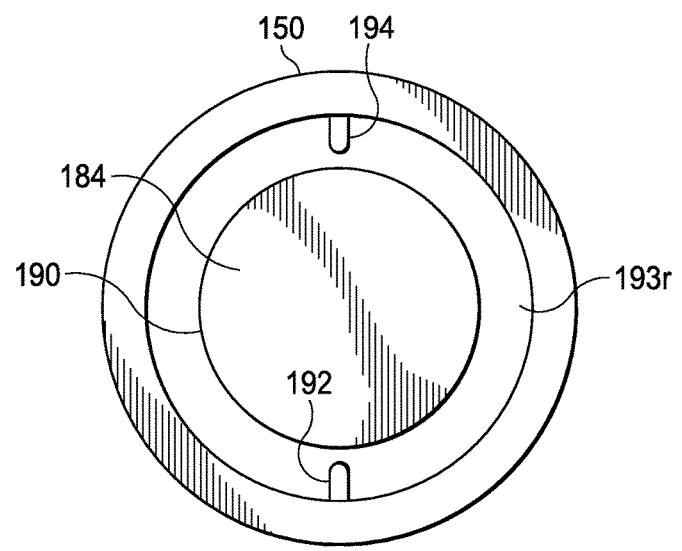
FIG. 6 illustrates a cross-sectional view of the imaging probe taken from line 6-6 of FIG. 3.

FIG. 6 shows an end view of the embodiment of FIG. 3, taken along line 6-6, where the movable actuating arms 192 and 194 are wires or strips coupled to a ring element 193r. In some embodiments, the actuating arms 192, 194 can be positioned in the space surrounding the elastomeric optical element 190 and the optical fiber 138 inside the cannula 150. In other embodiments, the actuating arms 192 and 194 can be positioned in openings, recesses, or grooves, formed within the cannula 150. Such embodiments allow the optical focusing element 152 to occupy all or a majority of the cross-section of the cannula 150. Embodiments with larger optical focusing elements 152 can achieve higher optical power and thus a smaller focus spot. Some embodiments may include only one movable actuating arm 192 or 194.

The ring element 193r can be positioned annularly around the elastomeric optical element 190 such that movement of the ring element 193r causes a corresponding deformation of the distal face 184 of the elastomeric element 190. In some embodiments, the ring element 193r can be a short cylinder or brace, attached to the side of the distal end portion of the elastomeric optical element 190. In others, the ring element 193r can be a substantially flat element with a large central opening in it for the focused imaging light to pass through. The flat ring element 193r can be positioned distally to the elastomeric optical element 190. In any of these embodiments, the actuating arms 192 and 194 can tilt the ring element 193 that causes a corresponding tilt of the distal face 184 of the elastomeric optical element 190.

The proximal ends of the actuating arms 192 and 194 can be actuated by the moving mechanism 179 that can selectively push or pull one or both of the actuating arms 192 and 194 toward or away from the distal end of the cannula 150 to selectively deform the elastomeric optical element 190. The moving mechanism 179 can be disposed near the proximal end of the imaging probe 130. In another embodiment, the moving mechanism can be disposed at the OCT system 124.

The distal end of the cannula 150 can include a transparent cover, e.g., a glass film or a plate, configured to prevent fluid from entering into the cannula 150.

Figure 7:
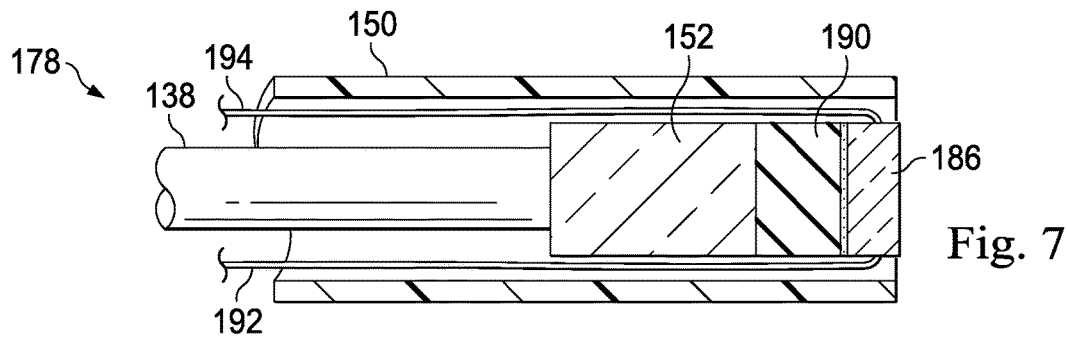
FIG. 7 illustrates a cross-sectional view of a distal portion of an imaging probe.

FIG. 7 is a cross-sectional view of the cannula 150, similar to the ones shown in FIGS. 3-6, but illustrating an embodiment of optical focusing element 152 that includes a distal window, or glass plate, 186. The distal window/glass plate 186 can be attached to the distal surface 184 of the elastomeric optical element 190 to maintain the shape of the distal surface 184 when the elastomeric optical element 190 is deformed. This distal window 186 can be useful because when the actuator system 178 deforms the elastomeric optical element 190, the distal surface 184 of the elastomeric optical element 190 may be distorted or curved. The distortion or curving of the distal surface 184 may cause the imaging quality to deteriorate. Embodiments with the distal window 186 may reduce or eliminate this unwanted distortion of the distal surface 184 of the elastomeric optical element 190.

The distal window 186 can be bonded to the distal surface 184 to keep the distal surface 184 in a desired shape, including a planar, convex, or concave shape. The distal window 186 can be a glass with an index of refraction similar to that of the elastomeric optical element 190. In some embodiments, the distal window 186 can be glass or some other rigid, transparent material with an index of refraction with a value lower than the refractive index of the elastomeric element 190 and higher than about 1.33, the index of refraction of water or the vitreous humor.

In some of these embodiments, the actuator system 178 can actuate the elastomeric optical element via the distal window 186. In these embodiments the actuating arms 192 and 194 can be attached to side walls or distal region of the distal window 186 instead of the elastomeric optical element 190. With this design, the elastomeric optical element 190 can be deformed or tilted by tilting the distal window 186 by the actuating arms 192 and 194.

Figure 8:
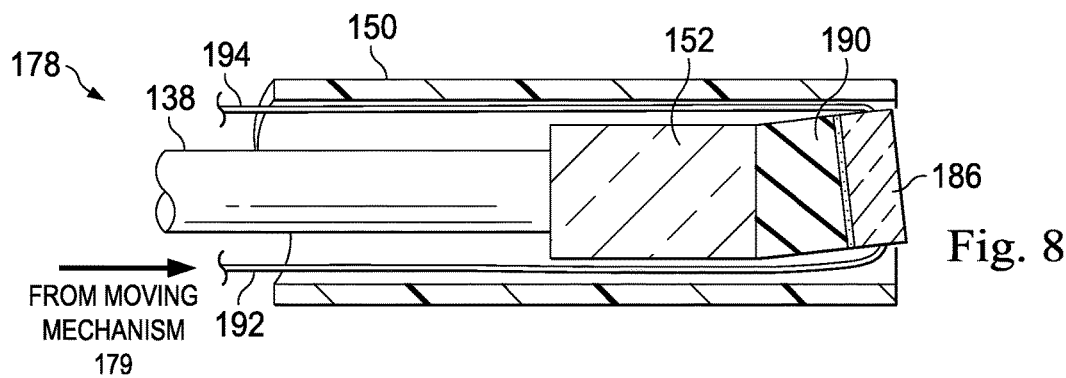
FIG. 8 illustrates a cross-sectional view of the distal portion of the imaging probe of FIG. 7.

FIG. 8 shows that the actuating arm 194 can be pulled toward the proximal end of the cannula 150 and the actuating arm 192 can be pushed toward the distal end of the cannula 150. As a result, the distal window 186 can be tilted upward. This will cause the elastomeric optical element 190 to correspondingly deform: compress in an upper region and expand in a lower region. The distal window 186 can likewise be tilted downward.

Figure 9:
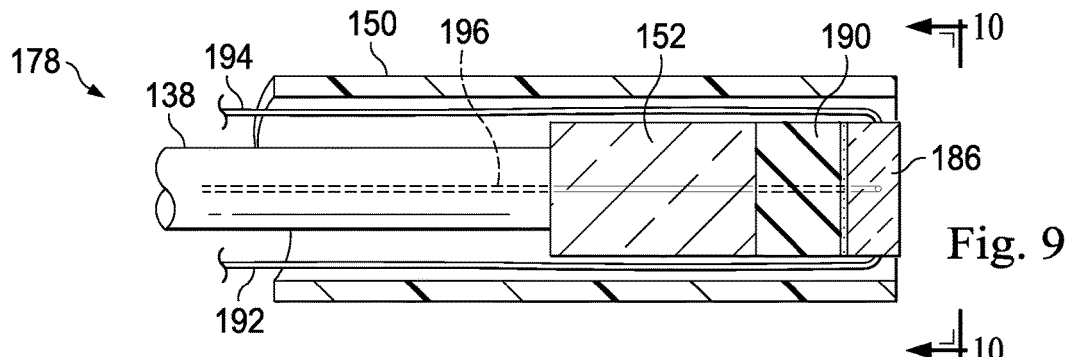
FIG. 9 illustrates a cross-sectional view of the distal portion of the imaging probe of FIG. 7.
Figure 10:
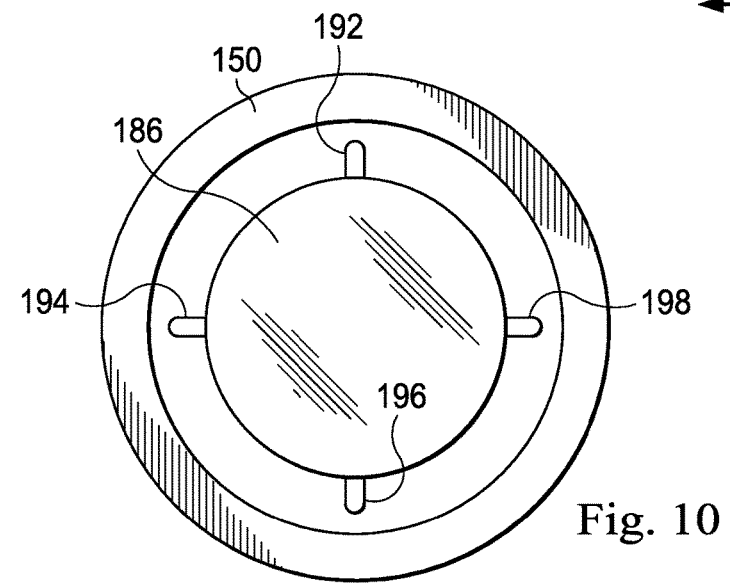
FIG. 10 illustrates an end view of the imaging probe taken from line 10-10 of FIG. 9.

FIG. 9 is a cross-sectional view of the cannula 150, similar to the ones shown in FIGS. 3-8, but illustrating an embodiment of actuator system 178 that includes additional actuating arms 196 and 198. FIG. 10 is an end view of the cannula 150 taken along a line 10-10 in FIG. 9.

As shown in FIG. 10, actuating arms 192, 194, 196 and 198 can be disposed evenly around the distal window 186, e.g., at 0°, 90°, 180°, and 270° around the circumference of the distal window 186. The actuating arms 192, 194, 196, and 198 can each be selectively pulled and pushed to tilt the distal window 186 with continuously varying tilting angles. Thus, the coordinated movement of the actuating arms 192, 194, 196, and 198 can tilt the distal window 186 to scan the focused imaging light not only along a scanning line, but along a wide variety of two-dimensional scanning patterns. These two-dimensional scanning patterns can include a spiral, a raster, a multi-petaled rose pattern, a multiple-radius pattern, a multiply folded path, and the like. The controller 126 can control the actuator system 178 to selectively actuate the actuating arms 192, 194, 196, and 198 to achieve any of these scanning patterns.

Analogous, four-actuating-wires embodiments exist without the distal window 186, corresponding to the embodiment of FIG. 3. Further, embodiments exist with different numbers of actuating arms. For example, some embodiments can have three actuating arms that are disposed at 0°, 120° and 240°. Visibly, these actuating arms are not disposed in an opposing manner. This three-actuating-arm embodiment can already be capable of scanning the focused imaging beam in a two-dimensional scanning pattern.

Figure 11:
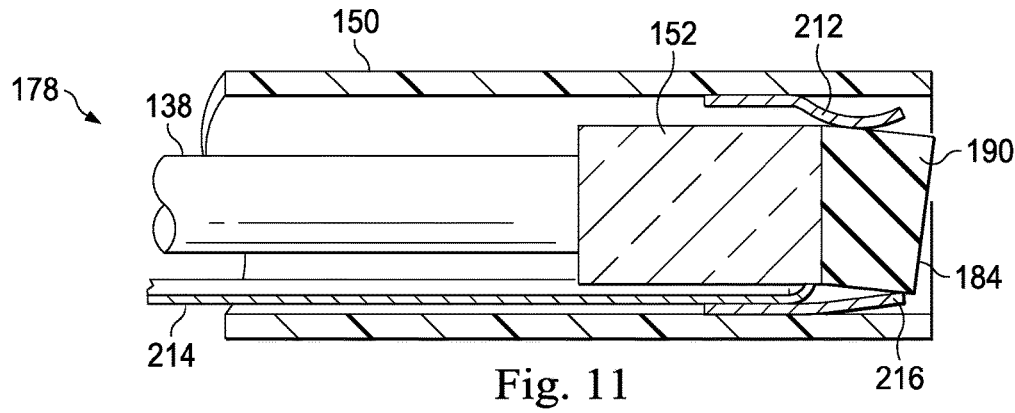
FIG. 11 illustrates a cross-sectional view of a distal portion of an imaging probe.

FIG. 11 is a cross-sectional view of the cannula 150, similar to FIGS. 3-5 and 7-9, illustrating a further embodiment of the actuator system 178 that includes a spring 212, an actuating arm 214, and a ramp 216. A proximal end of the spring 212 can be attached to an inner wall of the cannula 150. A distal end of the spring 212 can be bent toward the elastomeric optical element 190 to contact the elastomeric optical element 190. The spring 212 can be designed to exert an urging force on the elastomeric optical element 190. The urging force of the spring 212 can urge the elastomeric optical element 190 away from the spring 212, and toward the ramp 216.

Figure 12:
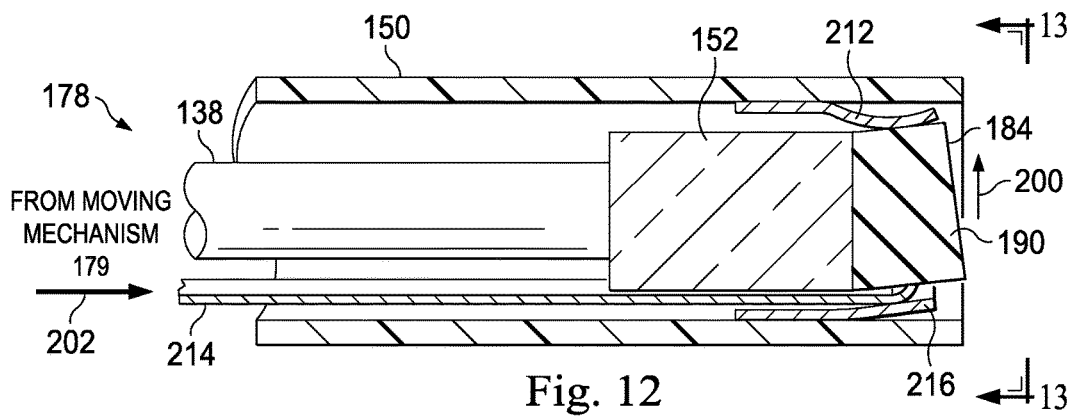
FIG. 12 illustrates a cross-sectional view of the distal portion of the imaging probe of FIG. 11.

As shown in FIG. 12, the actuating arm 214 and the ramp 216 can be disposed at the side of the elastomeric optical element 190 opposite to the spring 212. The actuating arm 214 can extend along the cannula 150. The proximal end of the actuating arm 214 can be pushed or pulled by an embodiment of the moving mechanism 179. The distal end of the actuating arm 214 can have a bend toward the elastomeric optical element 190. The proximal end of the ramp 216 can be attached to an inner wall of the cannula 150. The distal end of the ramp 216 can be bent toward the elastomeric optical element 190 to form a slope that gradually approaches the elastomeric optical element 190.

As shown in FIG. 12, when the actuating arm 214 is pushed by the moving mechanism 179 toward the distal end of the cannula 150 in a distal direction 202, the actuating arm 214 can slide on the ramp 216. The ramp 216 can guide the distal end of the actuating arm 214 toward the elastomeric optical element 190. In doing so, the ramp 216 can cause the distal end of the actuating arm 214 to push the elastomeric optical element 190 away from the ramp 216 and toward the spring 212. Depending on the position of the actuating arm 214 on the ramp 216, the pushing force exerted on the elastomeric optical element 190 can vary. For example, the further the actuating arm 214 is pushed toward the distal end of the ramp 216, the greater pushing force is exerted by the actuating arm 214 on the elastomeric optical element 190.

The urging force of the spring 212 opposes the pushing force of the actuating arm 214. When the biasing force of the spring 212 equals the pushing force of the actuating arm 214, the two forces can balance each other out and the elastomeric optical element 190 can be in a non-deformed state. When the elastomeric optical element 190 is in this non-deformed state, it may forward the focused imaging light without redirecting it.

As shown in FIG. 12, when the actuating arm 214 is pushed even further onto the ramp 216, the pushing force of the actuating arm 214 can increase to exceed the urging force of the spring 212. A resultant force from the interaction of the actuating arm 214 and the ramp 216 can push the distal end of the elastomeric optical element 190 in direction 200, towards the spring 212.

Summarizing FIGS. 11 and 12, as the moving mechanism 179 slides the actuating arm 214 along the ramp 216, the elastomeric optical element 190 can be deformed from an initial state bending towards the ramp 216 to a final state bending towards the spring 212. As the elastomeric optical element 190 deforms between these states, the focused imaging light is scanned along a scanning line.

Figure 13:
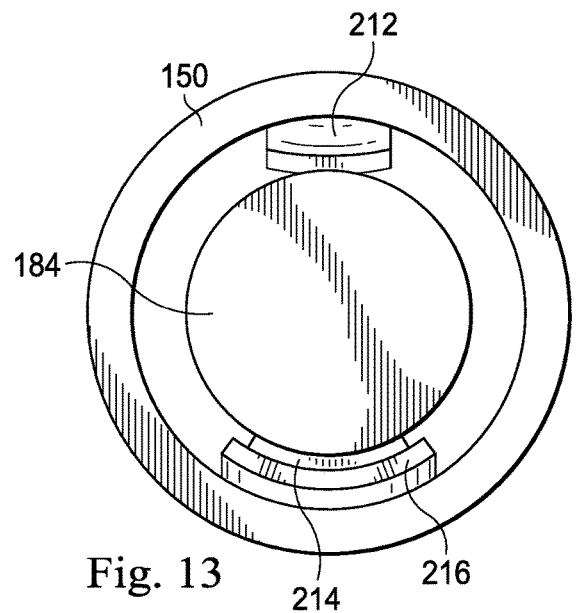
FIG. 13 illustrates an end view of the imaging probe taken from line 13-13 of FIG. 12.

FIG. 13 shows an end view of the cannula 150 taken along line 13-13 in FIG. 12. As shown, the spring 212 can include a plate or strip, having a curve with an apex of the curve contacting and exerting the urging force on the elastomeric optical element 190. The actuating arm 214 and the ramp 216 both can include a plate or strip with a curve conforming to the circumference of the elastomeric optical element 190.

A curved tip of the actuating arm 214 can move along a side wall of the elastomeric optical element 190 to deform the elastomeric optical element 190. The spring 212, the actuating arm 214, and the ramp 216 can be designed in a coordinated manner to deform the elastomeric optical element 190 to scan the focused imaging light along a vertical direction in the orientation shown in FIG. 13.

In another embodiment, a second deforming unit that includes a second spring, actuating arm, and ramp can be disposed at opposing sides of the elastomeric optical element 190, in a direction about right angle with the first deforming unit of the spring 212, actuating arm 214 and ramp 216. These two deforming units are capable of scanning the focused imaging light not only along a single scanning line, but along two dimensional scanning patterns. As before, embodiments with more than two deforming units can also be designed.

Finally, in some embodiments, the optical focusing element 152 and the elastomeric optical element 190 can be one integrated optical element.

Embodiments as described herein may provide an imaging probe having an actuator that utilizes an elastomeric optical element to scan a focused imaging light of the imaging probe along a scanning pattern. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:
1. An imaging probe, comprising
a housing, having a proximal region configured to be coupled to an optical cable;
a cannula, extending from a distal region of the housing;
an optical guide, positioned partially in the housing and partially in the cannula, configured
to receive an imaging light from the optical cable in the proximal region of the housing, and
to guide the imaging light towards a distal end of the cannula;
an optical focusing element, configured
to receive the imaging light from the optical guide, and
to emit a focused imaging light;
a transparent elastomeric optical element, configured
to receive the focused imaging light from the optical focusing element, and
to be deformable to redirect the focused imaging light passing, through the elastomeric optical element; and
an actuator system, configured to deform the elastomeric optical element to redirect the focused imaging light.
2. The imaging probe of claim 1, wherein:
the optical cable and the optical guide are portions of one continuous optical guidance system.
3. The imaging probe of claim 1, wherein:
the optical focusing element comprises a Gradient Index (GRIN) lens.
4. The imaging probe of claim 1, wherein:
the elastomeric optical element comprises one or more of a silicone material, an elastomer, a polymer, an epoxy, a polyurethane material, a gel, and an electro-active polymer.
5. The imaging probe of claim 1, wherein:
the elastomeric optical element comprises nanoparticles.
6. The imaging probe of claim 5, wherein:
the nanoparticles comprise Ti02.

7. The imaging probe of claim 1, wherein:
the elastomeric optical element has an index of refraction higher than 1.4.

8. The imaging probe of claim 1, the actuator system comprising:
at least one actuating arm, having
a distal end, coupled to the elastomeric optical element, and
a proximal end, coupled to a moving mechanism, wherein
the moving mechanism is configured to at least one of push and pull the proximal end of the at least one actuating arm so that the distal end of the at least one actuating arm selectively compresses and expands the elastomeric optical element.

9. The imaging, probe of claim 8, the actuator system comprising:
two actuating arms; and
the moving mechanism is configured to move the two actuating arms in an opposing manner so that they together deform the elastomeric optical element.

10. The imaging probe of claim 1, wherein:
a numerical aperture of the focused imaging light is greater than a numerical aperture of the optical guide.

11. The imaging probe of claim 1, wherein:
a diameter of a focal spot of the focused imaging light is less than 50 microns.

12. The imaging probe of claim 1, the actuator system comprising:
a ring element, positioned at a distal region of the elastomeric optical element; and
at least one movable actuating wire, positioned inside the cannula, and coupled to the ring element, configured to be able to tilt a distal face of the elastomeric optical element.

13. The imaging probe of claim 1, comprising:
a distal window,
disposed at a distal end of the elastomeric optical element, and
configured to maintain the shape of a distal surface of the elastomeric optical element, wherein
the distal window comprises at least one of glass and a rigid transparent material.

14. The imaging probe of claim 13, wherein:
the distal window has an index of refraction lower than an index of refraction of the elastomeric optical element and higher than an index of refraction of water.

15. The imaging probe of claim 1, wherein:
the actuator comprises a spring, a ramp, and an actuating arm configured to deform at least a portion of the elastomeric optical element.

16. The imaging probe of claim 15, wherein:
the actuating arm is translatable with respect to the ramp.

17. The imaging probe of claim 15, wherein:
the spring and the ramp are positioned on opposite sides of the elastomeric optical element.

18. The imaging probe of claim 1, wherein:
the actuator is configured to actuate the elastomeric optical element to scan the focused imaging light along a scanning pattern having a linear extent between 1 mm and 5 mm at a distance between 5 mm and 10 mm from a distal end of the elastomeric optical element.

19. The imaging probe of claim 1, wherein:
the actuator is configured to actuate the elastomeric optical element to scan the focused imaging light along a two-dimensional scanning pattern extending in two directions.

20. The imaging probe of claim 19, wherein:
the two dimensional scanning pattern comprises one or more of a spiral, a raster, a constant-radius asterisk pattern, a multiple-radius asterisk pattern, a multi-petaled rose pattern, and a multiply folded path.

21. The imaging probe of claim 19, wherein:
the actuator comprises at least two sets of actuating mechanisms configured to deform the elastomeric optical element in at least two directions.

22. The imaging probe of claim 1, wherein
the optical focusing element and the elastomeric optical element are one integrated optical element.

23. The imaging probe of claim 1, wherein:
a position of the optical guide remains steady relative to the optical focusing element during a scanning operation of the imaging probe.

24. An imaging probe, comprising
a housing, having a proximal region configured to be coupled to an optical cable;
a cannula, extending from a distal region of the housing;
an optical guide, positioned partially in the housing and partially in the cannula, configured
to receive an imaging light from the optical cable in the proximal region of the housing, and
to guide the imaging light towards a distal end of the cannula;
an optical focusing element, configured
to receive the imaging light from the optical guide, and
to emit a focused imaging light;
an elastomeric optical element, configured
to receive the focused imaging light from the optical focusing element, and
to be deformable to redirect the focused imaging light; and
an actuator system, configured to deform the elastomeric optical element to redirect the focused imaging light, wherein the actuator system comprises a flexible strip bent into a U-shape, having
two strip segments connecting, to an apex of the U-shape, at least one of the strip segments being movable,
the apex of the U-shape being positioned at a distal end of the cannula, and
an opening being formed at the apex of the U-shape; and
a distal face of the elastomeric optical element is affixed to the apex of the U-shape, so configured that
the focused imaging light leaves the elastomeric optical element through the opening, and
the elastomeric optical element is deformed when at least one of the strip segments is actuated.

25. The imaging, probe of claim 24, wherein:
a first strip segment is movable,
a second strip segment is fixed to an inner side of the cannula, and
the actuator system is configured to deform the elastomeric optical element by moving the movable first strip segment.

26. The imaging probe of claim 25, wherein:
a proximal portion of the movable strip segment is expanded into an inner actuator cannula, movable within the cannula; and
a groove is formed on the side of the actuator cannula to accommodate the fixed strip segment.

27. An imaging probe, comprising
a housing, having a proximal region configured to be coupled to an optical cable;

a cannula, extending from a distal region of the housing;

an optical guide, positioned partially in the housing and partially in the cannula, configured
- to receive an imaging light from the optical cable in the proximal region of the housing, and
- to guide the imaging light towards a distal end of the cannula;

an optical focusing element, configured
- to receive the imaging light from the optical guide, and
- to emit a focused imaging light;

an elastomeric optical element, configured
- to receive the focused imaging light from the optical focusing element, and
- to be deformable to redirect the focused imaging light; and an actuator system, configured to deform the elastomeric optical element to redirect the focused imaging light, the actuator system comprising:

a flexible strip bent into a U-shape, having
- a movable strip segment and a fixed strip segment, connecting to an apex of the U-shape,
- the apex of the U-shape being positioned at a distal end of the cannula, and
- an opening being formed at the apex of the U-shape; and an inner actuator cannula, movably disposed inside the cannula; wherein
- the movable strip segment is coupled to the inner actuator cannula,
- the fixed strip segment is coupled to fixed inner cannula segment, fixed to an inner wall of the cannula, and
- the inner actuator cannula includes a groove to accommodate the fixed inner cannula segment.

* * * * *